US008177950B2

(12) United States Patent
Thompson et al.

(10) Patent No.: US 8,177,950 B2
(45) Date of Patent: May 15, 2012

(54) THERMORESPONSIVE MICROPARTICLE COMPOSITE HYDROGELS FOR ELECTROPHORESIS

(75) Inventors: Jeffery W. Thompson, Lafayette, TN (US); Holly Stretz, Cookeville, TN (US); Pedro E. Arce, Cookeville, TN (US)

(73) Assignee: Tennessee Technological University, Cookeville, TN (US)

( * ) Notice: Subject to any disclaimer, the term of this patent is extended or adjusted under 35 U.S.C. 154(b) by 628 days.

(21) Appl. No.: 12/275,253

(22) Filed: Nov. 21, 2008

(65) Prior Publication Data

US 2009/0127116 A1 May 21, 2009

Related U.S. Application Data

(60) Provisional application No. 60/989,493, filed on Nov. 21, 2007.

(51) Int. Cl.
*G01N 27/447* (2006.01)
(52) U.S. Cl. ......... 204/469; 204/470; 424/486; 424/487
(58) Field of Classification Search .................. 424/486, 424/487; 204/469, 470
See application file for complete search history.

(56) References Cited

U.S. PATENT DOCUMENTS

| | | | |
|---|---|---|---|
| 6,030,634 A * | 2/2000 | Wu et al. | 424/423 |
| 6,414,043 B1 | 7/2002 | Asher | |
| 6,770,698 B1 | 8/2004 | Chu | |
| 7,399,396 B2 | 7/2008 | Barron | |
| 2002/0001571 A1 * | 1/2002 | Wu et al. | 424/61 |
| 2005/0175702 A1 * | 8/2005 | Muller-Schulte | 424/486 |
| 2006/0074186 A1 | 4/2006 | Barron | |
| 2007/0092560 A1 | 4/2007 | Sukuru | |

FOREIGN PATENT DOCUMENTS

WO  WO2008079280 A1  7/2008

OTHER PUBLICATIONS

Soddlemann et al., Prog. Colloid Polym. Sci, 129, 88-94, 2004.*
Brownsey JJ, Noel TR, Parker R, and Ring SG. "The glass transition behavior of the globular protein bovine serum albumin," Biophysical Journal, 2003;85:3943-3950.
Huang G and Hu Z. "Phase behavior and stabilization of microgel arrays," Macromolecules, 2007;40:3749-3756.
Huang G, Zhang Y, Ouyang J, Baeyens WRG, and Delanghe JR. "Application of carbon nanotube-matrix assistant native polyacrylamide gel electrophoresis to the separation of apolipoprotein A-I and complement C3," Analytica Chimica Acta, 2006;557(1-2):137-145.
Ishida N and Biggs S. "Direct observation of the phase transition for a poly(N-isopropylacrylamide) layer grafted onto a solid surface by AFM and QCM-D," Langmuir, 2007;23:11083-11088.

(Continued)

*Primary Examiner* — Satya Sastri
(74) *Attorney, Agent, or Firm* — Baker, Donelson, Bearman, Caldwell & Berkowitz, PC

(57) ABSTRACT

Disclosed are thermoresponsive microparticle composite hydrogels comprising poly(N-isopropyl acrylamide) and polyacrylamide, and methods regarding their manufacture and their use. The present invention provides in one aspect a thermoresponsive microparticle hydrogel, wherein the matrix morphology is controllably and selectively altered by incorporation of thermoresponsive nano/micro-particles. The particles are preferably poly(N-isopropyl acrylamide) particles. The present invention also provides methods of making and using such hydrogels.

30 Claims, 7 Drawing Sheets

OTHER PUBLICATIONS

Lyon LA, Debord JD, Debord SB, Jones CD, McGrath JG, and Serpe MJ. "Microgel colloidal crystals," J. Phys. Chem. B, 2004:108;19099-19108.

Ma X, Sauer JA, and Hara M. "Poly(methyl methacrylate) based ionomers. 1. DynamicMechanical Properties and Morphology," Macromolecules, 1995;28:3953-3962.

Matos MA. "Electroosmotically enhanced mass transfer through polyacrylamide gels," Journal of Colloids and Interface Science. 2006;300(1):429-436.

McGrath JG, Bock RD, Cathcart M, and Lyon AL. "Self-assembly of 'paint-on' colloidal crystals using poly(styrene-co-N-ispropylacrylamide) spheres," Chemistry of Materials, 2007;19:1584-1591.

Meng Z, Cho JK, Debord S, Breedveld V, and Lyon LA. "Crystallization behavior of soft, attractive microgels," J. Phys. Chem. B, 2007;111(25):6992-6997.

Muniz EC and Geuskens G. "Polyacrylamide hydrogels and semi-interpenetrating networks (IPNs) with poly(N-isopropylacrylamide): Mechanical properties by measure of compressive elastic modulus." J. Mater. Sci: Mater. Med., 2001;12:879-881.

Musch J, Schneider S, Lindner P, and Richtering W. "Unperturbed volume transition of thermosensitive poly-(N-isopropylacrylamide) microgel particles embedded in a hydrogel matrix." J Phys. Chem. B, 2008;112,6309-6314.

Nayak S, Gan D, Serpe MJ, and Lyon AL. "Hollow thermorsponsive microgels," Small, 2005;1:416-421.

Nolan CM, Reyes CD, Debord JD, Garcia AJ, and Lyon AL. "Phase transition behavior, protein adsorption and cell adhesion resistance of poly(ethylene glycol) cross-linked microgel particles," Biomacromolecules, 2005;6:2032-2039.

Okay O and Opperman W. "Polyacrylamide-clay nanocomposite hydrogels: rheological and light scattering characterization," Macromolecules, 2007;40:3378-3387.

Okubo M, Azume I, and Yamamoto Y. "Preferential adsorption of BSA dimer onto polymer microspheres having a heterogeneous surface consisting of hydrophobic and hydrophilic parts," Colloid and Polymer Science, 1990;268:598-603.

Pascal JA, O'Hara R, Oyanader MA, and Arce P. "Optimal separation times for electrical field flow fractionation with couette flows," Biomicrofluidics, submitted for review, 2007.

Pascal JA, Stretz HA, Oyanader MA, and Arce PE, "Electrohydrodynamics in nanoparticle embedded gels: effects of morphology and electrostatic potential," presented at AIChE National Conference Proceedings, Salt Lake City, Utah, Nov. 4-9, 2007.

Plunkett KN, Zhu X, Moore JS, and Leckband DE, "PHIPAM chain collapse depends on the molecular weight and grafting density," Langmuir, 2006;22:4259-4266.

Rill RL, Lock BR, Liu Y, Dharia J, and Van Winkle D. "Protein electrophoresis in polyacrylamide gels with templated pores," Electrophoresis, 1996;17(8):1304-12.

Sedrick HE, Bollig JR, Stretz HA, and Arce P. "Nanoparticle-Composite Gels for Protein Separation: Characterization Based on Acoustic Methods," presented at AIChE Annual Conference, Salt Lake City, Utah, Nov. 4-9, 2007.

Sedrick HE, Burns NA, Bollig JR, Stretz H, and Arce PE. "Nanoparticle-composite gels for protein separation: Synthesis and preliminary characterization," abstract, ACS 235 Colloids Division, Apr. 6-10, 2008.

Sierra-Martin B, Romero-Cano MS, Fernández-Nieves A, and Fernández-Barbero A. "Thermal control over the electrophoresis of soft colloidal particles," Langmuir, 2006;22:3586-3590.

Soddeman M and Richtering W. "Hydrogels filled with thermosensitive microgel particles," Progr. Colloid. Polym. Sci., 2004;129:88-94.

St. John AN, Breedveld V, and Lyon AL. "Phase behavior in highly concentrated assemblies of microgels with soft repulsive interaction potentials," Journal of Physical Chemistry B, 2007;111(27):7796-7801.

Suzuki D, McGrath JG, Kawaguchi H, and Lyon AL. "Colloidal crystals of thermosensitive core/shell hybrid microgels," Journal of Physical Chemistry C, 2007;111:5667-5672.

Tanaka T. "Gels," Scientific American, 1981;244:124-136.

Trinh S, Locke BR, and Arce P. "Diffusive-convective and diffusive-electroconvective transport in non-uniform channels with application to macromolecular separations," Separation and Purification Technology, 1999;15:255-269.

Wang J and Ugaz VM. "Using in situ rheology to charcterize the microstructure in photopolymerized polyacrylamide gels for DNA electrophoresis," Electrophoresis, 2006;27:3349-3358.

Yang C, Li D, and Masliyah J. "Modeling forced liquid convection in rectangular microchannels with electrokinetic effects," International Journal of Heat and Mass Transfer, 1998;41:4229-4249.

Zhang Q-S, Zha L-S, Ma J-H, and Liang B-R. "Synthesis and characterization of novel, temperature-sensitive microgels based on N-isopropylacrylamide and tert-butyl acrylate," Journal of Applied Polymer Science, 2007; 103:2962-2967.

Yoshioka H, Mori Y, and Tsuchida E. "Crosslinked poly(isopropylacrylamide) gel for electrophoretic separation and recovery of substances," Polymers for Advanced Technologies, 1994;5(4):221-224.

International Search Report from PCT/US2008/084352 (Jul. 20, 2009).

* cited by examiner

THERMORESPONSIVE MICROPARTICLE COMPOSITE HYDROGELS FOR ELECTROPHORESIS

CROSS-REFERENCE TO RELATED APPLICATIONS

This Non-Provisional Patent Application, filed under 35 U.S.C. §111(a), claims the benefit under 35 U.S.C. §119(e)(1) of U.S. Provisional Patent Application No. 60/989,493, filed under 35 U.S.C. §111(b) on 21 Nov. 2007, and which is hereby incorporated by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON COMPACT DISC

Not applicable.

BACKGROUND OF THE INVENTION

1. Field of the Invention

The present invention relates to separation of macromolecules (e.g., proteins and nucleic acids) via electrophoresis.

2. Description of Related Art

Polymer hydrogels have played an instrumental role in the separation of both proteins and DNA, as these materials are needed for use in medical diagnostics, drug purification, and other scientific research (see, e.g., Sukuru, Karunakar, "Lipophilic Vehicle-Based Dual Controlled Release Matrix System"; U.S. Patent App. Pub. No. 2007/0092560, filed 26 Oct. 2006; and Wilson Moya, Jad, Jaber, "Purification of Proteins" PCT App. Pub No. WO2008079280, filed 20 Dec. 2007, each of which is hereby incorporated by reference in its entirety). These separations are performed using an applied electrical field in a process known as electrophoresis (see, e.g., Probstein, Robert. *Physicochemical Hydrodynamics: An Introduction.* 2d ed, hereby incorporated by reference in its entirety). Electrophoresis is a separation technique for separating proteins or nucleic acids on the basis of both their charge density and their molecular weight, and is often performed in a hydrogel matrix. Two transport parameters determine these molecular level characteristics: the electrophoretic mobility; and the effective molecular diffusivity. The results of the separation are often termed "fuzzy" meaning that the process does not effectively or sufficiently separate or resolve the proteins in such a mixture. The problem, then, is one of obtaining better resolution and better separation in such cases. Many techniques are currently used to improve separation efficiency. One of the most promising approaches is to modify the morphology of the hydrogel matrix. In using a polymeric gel, there are five major experimental variables one might consider to produce a more complete separation. One can change, for example, the concentration ratio of the matrix monomer and its cross-linker (which affects the porosity of the matrix), the pH and amount of the buffer that makes up the fluid phase, the system temperature, the electrical field applied to the solute, and the shear applied to the system. Adjustment of these variables can improve separation between two solutes based on both size differences (size selectivity or molecular sieving) and charge differences, which will modify either or both the electrophoretic mobility and/or the molecular diffusivity.

The introduction of nanotechnology has recently contributed improvements to electrophoretic separation techniques. By using nano-templates, molecules that segregate particular morphological structures during gel synthesis, and removing these templates post synthesis, new gel morphologies can be created. In Rill, et al's work, both DNA seed molecules as well as Sodium Dodecyl Sulfate (SDS) were used as templates (see, e.g., Dharia J R, Pill R, Van Winkle D, Locke B R, and Arce P, "Preparation and characterization of polyacrylamide gels containing microchannels." American Chemical Society Annual Meeting, Orlando, Fla., May 5-7, 1994; and Rill R, Locke B R, Liu Y, Dharia J, and Van Winkle D, "Protein electrophoresis in polyacrylamide gels with templated pores." Electrophoresis, 1996; 17(8):1304-1312, each of which is hereby incorporated by reference in its entirety). The reported results of that work suggested that separation efficiency could be improved in these gels templated with SDS. Trinh et. al used idealized geometric models to simulate Rill's results (S. Trinh, B. R. Locke, and P. Arce, "Diffusive-convective and diffusive-electroconvective transport in non-uniform channels with application to macromolecular separations," Separation and Purification Technology, vol. 15, pp. 255-269, 1999, hereby incorporated by reference in its entirety). The results of Trinh's study suggest that the morphology of the gel plays an important role in modifying transport of macromolecules and improving electrophoretic separations.

More recently, nanoparticle insertion into hydrogels proved useful when regular, unmodified polyacrylamide gels failed (Huang Guangming, Zhang Yangjun, Ouyang Jin, Baeyens Willy R. G. Delanghe Joris R. "Application of carbon nanotube-matrix assistant native polyacrylamide gel electrophoresis to the separation of apolipoprotein A-I and complement C3." Analytica Chimica Acta. 557. 2006. 137-145, hereby incorporated by reference in its entirety). In addition, Matos et. al, has reported important changes in electrokinetic based fluxes across modified gels with silica-based nanoparticle insertion (Matos M, Tilton R and White L. "Electroosmotically enhanced mass transfer through polyacrylamide gels." Journal of Colloids and Inferface Science. Volume 300 Issue 1. Aug. 1, 2006. 429-436, hereby incorporated by reference in its entirety). These studies collectively, show that gel structure can effectively be modified by adding a third component: nanoparticles.

None of the hydrogels in the prior art, however, teach a composite hydrogel matrix comprising a thermoresponsive component in combination with electrophoretic transport. Neither do any hydrogels of the prior art teach a gel therein the matrix morphology may be modified selectively and/or regionally.

The technical problem underlying the present invention was therefore to overcome these prior art difficulties by creating a tunable composite gel that would be effective and useful for electrophoretic studies of solute mobility in narrow channel/wide channel geometry/matrix morphology. The solution to this technical problem is provided by the embodiments characterized in the claims.

BRIEF SUMMARY OF THE INVENTION

The present invention is a thermally-responsive microparticle copolymer hydrogel for the efficient separation of charged biomolecules via electrophoresis, and methods of using the same.

The present invention provides a thermoresponsive microparticle hydrogel, wherein the matrix morphology is controllably and selectively altered by incorporation of a thermoresponsive nano/micro-particle. The particle may or may not be grafted to the matrix polymer (including, but not limited to, acrylamide, acrylic acid, and folate—see, e.g., Lyon L A, Debord J D, Debord S B, Jones C D, McGrath J G, and Serpe M J. "Microgel colloidal crystals," J. Phys. Chem. B. 2004: 108; 19099-19108; Nayak S, Lee H, Chmielewski J, and Lyon L A. "Folate-mediated cell targeting and cytotoxicity using thermoresponsive microgels," J. Am. Chem. Soc. 2004; 126:10258-10259; and Meng Z, Cho J K, Debord S, Breedveld V, and Lyon L A. "Crystallization behavior of soft, attractive microgels," J. Phys. Chem. B, 2007; 111:6992-6997, each of which is incorporated by reference herein in its entirety). The introduction of a co-monomer into the matrix polymer would cause bulk changes in volume with application of external stimuli (temperature), and the composite will instead exhibit microscopic/nanoscopic changes in morphology with application of external stimuli. Introducing this co-monomer, the co-monomer being already polymerized into discrete particles, though, advantageously alters the physical morphology of the gel matrix in a selectively tunable or controllable fashion by modifying operating parameters including but not limited to temperature, pressure, and shear, as well as preparation parameters such as microparticle size, shape, and concentration. Hydrogels, by weight, are mostly liquid and so their densities are similar to those of liquids, yet they behave like solids because of the addition of a gelling agent (e.g., a crosslinker), producing a three-dimensional network of polymer chains (e.g., polyacrylamide) that spans the volume of the liquid medium. This three-dimensional network is usually referred to as the "matrix" or the "gel matrix."

The present invention also provides methods of tuning the morphology of the matrix, thus creating the opportunity to create changes in matrix porosity, which then creates selectivity differences based on the molecular sieving (mentioned earlier) and the electrophoretic mobility. The co-monomer used is N-isopropyl acrylamide (NIPAM) which—in its polymerized form (poly-(N-isopropyl acrylamide), or PNIPAM)—offers a radical, reversible, and thermosensitive change in volume when dispersed in aqueous media. PNIPAM particles will shrink drastically above a given temperature, shedding aqueous solution in the process. Beyond simply demonstrating the effects on electrophoretic separation efficiency of nanoparticles added to a stable gel matrix, the present invention demonstrates selectivity when one component of the matrix phase—the PNIPAM particles—undergoes this drastic morphological change. One such example would be to ask if there was any appreciable difference in the two forms of the nanoparticle that would lead to a greater improvement in separation.

The inventors have been interested in the concept of hydrogel morphology, and specifically the effects of a bimodal distribution of gel porosity on optimal time to separation. Mathematical models have been and are being developed to explore certain possibilities in separations of charge particles such as proteins available exposed to different fields, including regimes where the driving force is hydrodynamic flow and/or electrophoretic flow. Various studies have shown that optimal time of separation can be achieved by a variety of different ways including geometrical modifications of gel morphology. Of particular interest here is a model published by Trinh et. al, 1999 for non-uniform channels. Their assumed geometry is shown below in FIGS. 1A, 1B, and 1C. These authors concluded that "by appropriately selecting the flowrate . . . or the electrical field strength . . . an optimum time of separation can be determined for separation of two comparably sized molecules whose sizes are close to those of the narrower part of the pore."

In a gel matrix, one effective way to experimentally create a bimodal dispersion of channels (see, e.g., FIGS. 1A, 1B, and 1C) having dimensions on the order of nanometers (nm) is to utilize the intrinsic pore size of the crosslinked hydrogel for the narrowest channels and to induce or template the larger pore sizes by forming a composite. The narrow channels would be interspersed with volume elements in which OSA feels no restriction (for example, porosities on the order of microns). One way to achieve this morphology is to appropriately disperse nanoparticles within the matrix of a traditional gel, yielding a composite gel. At a certain concentrations, the nanoparticles will exhibit some interparticle distance on the order of nanometers or microns. In addition, all polymer hydrogels have some inherent porosity determined by crosslink density and solvent factors (see, e.g., V. M. Ugaz and J. Wang, "Using in situ rheology to characterize the microstructure in photopolymerized polyacrylamide gels for DNA electrophoresis," Electrophoresis, vol. 27, pp. 3349-3358, 2006, hereby incorporated by reference in its entirety). Thus, the composite gel would have two potential ways to control porosity (dual porosity): nanoparticle interparticle distance; and inherent gel porosity. This view of the system assumes that OSA or any protein within the gel cannot move through the space occupied by the particle itself. It also assumes that OSA is globular. (Note that Brownsey et al. have recently published information showing that BSA, for instance, is roughly a globular equilateral triangular prism with sides of 8 nm and a depth of 3 nm (J. J. Brownsey, T. R. Noel, R. Parker, and S. G. Ring, "The glass transition behavior of the globular protein bovine serum albumin," Biophysical Journal, vol. 85, pp. 3943-3950, 2003, hereby incorporated by reference in its entirety)).

Charged Laponite (a synthetic clay) nanoparticles have been inserted into a polyacrylamide matrix by Sedrick (Sedrick H. E. N. A. Burns, J. R. Bollig, H. Stretz, P. E. Arce. "Nano-composite gels for protein separation: Synthesis and preliminary characterization". ACS 235 Colloids Division 2008, hereby incorporated by reference in its entirety). The results of those studies are not yet clear because the presence of the Laponite nanoparticles seems to interfere with the crosslinking, such that the two pore size distributions cannot be controlled separately (H. E. Sedrick, J. R. Bollig, H. A. Stretz, and P. Arce, "Nanoparticle-Composite Gels for Protein Separation: Characterization Based on Acoustic Methods," presented at AIChE Annual Conference, Salt Lake City, Utah, 2007, hereby incorporated by reference in its entirety). This new phenomenon appears not to have been reported in the literature for this type of nanoparticle. Other types of silica nanoparticles, though, have been reported to disperse in gel materials successfully (see, e.g., Matos et al., 2006).

The present inventors' approach instead attempted to insert uncharged organic microparticles into a gel. The particles themselves can shrink, leaving holes—pores, and sometimes referred to herein as "voids"—on the order of 200 to 400 nm in diameter within and bounded by the polyacrylamide template. If the crosslinker in a polyacrylamide gel is adjusted, as was reported by Ugaz and Wang, 2006, the intrinsic porosity can be adjusted down to 4-12 nm, representing a narrower restrictive channel. The present inventors' new approach is like a photo "negative" of the Laponite approach. Here, the morphology is tunable because one can create a wider channel by adjusting a simple process variable, temperature, in addition to the nanoparticle concentration inside the hydrogel material. All of these efforts attempt to recreate the sieving-like effect that can be achieved by producing a gel with a dual porosity.

The present inventors demonstrate herein that tunable poly-N-isopropyl acrylamide (PNIPAM) particles were synthesized, and that the volume phase transition they undergo with a simple change in temperature can be characterized visually. Further, conformational changes can be observed using simple scan techniques on a UV/Vis spectrophotometer. The PNIPAM particles were mechanically mixed into an acrylamide matrix gel solution which was subsequently cross-linked. Finally, separation characteristics of control (without PNIPAM) versus composite (with PNIPAM) gels were compared at two different temperatures—wherein the upper temperature produces PNIPAM morphology in which the PNIPAM particles have shrunk and left pores in the matrix gel—and with two proteins (ovine serum albumin, "OSA"; and bovine serum albumin, "BSA") of different molecular weights.

In one embodiment, the invention is a composite hydrogel, wherein the hydrogel comprises a matrix and a plurality of thermoresponsive microparticles. In one aspect of this embodiment, the matrix envelops substantially all of the thermoresponsive microparticles, the thermoresponsive microparticles may be dispersed substantially uniformly throughout the matrix, and the matrix may be a polyacrylamide matrix. In this aspect, the thermoresponsive microparticle has a first diameter within a first temperature range, and a second diameter within a second temperature range, wherein the first diameter is greater than the second diameter and wherein the first temperature range is below the second temperature range. Also in this aspect, the first temperature range is between 0° C. and 31° C. and the second temperature range is from 31° C. to 60° C. In this aspect, the hydrogel further comprises voids when the second temperature range is between 31° C. and 60° C. In a preferred aspect of this embodiment, the thermoresponsive microparticles are PNIPAM particles. Preferably, the thermoresponsive microparticles represent between greater than zero and 40% of the hydrogel by weight. More preferably, the thermoresponsive microparticles represent between greater than zero and 10% of the hydrogel by weight. Most preferably, the thermoresponsive microparticles represent between greater than zero and 4% of the hydrogel by weight. Preferably, N,N'-methylene-bis-acrylamide (Bis) represents between greater than zero and 10% of the hydrogel by weight. More preferably, Bis represents between greater than zero and 6% of the hydrogel by weight. Most preferably, Bis represents between 2% and 6% of the hydrogel by weight.

In a second embodiment, the invention is a method of making a thermoresponsive hydrogel, comprising the steps of: a) selecting thermoresponsive microparticles having a first diameter within a first temperature range, and a second diameter within a second temperature range; b) providing acrylamide, bis-acrylamide, a radical-producing agent, a chemical initiator, and water; c) mixing the microparticles, acrylamide, bis-acrylamide, and water; d) adding the radical-producing agent to the mixture, then adding the chemical initiator to the mixture. In a preferred aspect of this embodiment, the first diameter is greater than the second diameter, and the first temperature range is below the second temperature range. In a more preferred aspect, the first temperature range is between 0° C. and 31° C. and the second temperature range is from 31° C. to 60° C. In a most preferred aspect of this embodiment, the thermoresponsive microparticles are PNIPAM particles, the radical-producing agent is ammonium persulfate, and the chemical initiator is N,N,N',N'-tetramethylethylenediamine. Preferably, the thermoresponsive microparticles represent between greater than zero and 40% of the hydrogel by weight. More preferably, the thermoresponsive microparticles represent between greater than zero and 10% of the hydrogel by weight. Most preferably, the thermoresponsive microparticles represent between greater than zero and 4% of the hydrogel by weight. Preferably, N,N'-methylene-bis-acrylamide (Bis) represents between greater than zero and 10% of the hydrogel by weight. More preferably, Bis represents between greater than zero and 6% of the hydrogel by weight. Most preferably, Bis represents between 2% and 6% of the hydrogel by weight.

In a third embodiment, the invention is a method of detecting a biomolecule, comprising the steps of: a) obtaining a thermoresponsive hydrogel comprising a matrix and a plurality of thermoresponsive microparticles, wherein the matrix envelops substantially all of the thermoresponsive microparticles, the thermoresponsive microparticles are dispersed substantially uniformly throughout the matrix, and wherein the thermoresponsive microparticles have a first diameter at a first temperature range and a second diameter at a second temperature range; b) subjecting the hydrogel to a first temperature; c) applying to the hydrogel a solution, wherein the solution comprises at least one biomolecule to be detected; d) applying an electric field to the hydrogel; e) subjecting the hydrogel to a second temperature; f) removing the hydrogel from the electric field; and g) detecting the at least one biomolecule. In a preferred aspect of this embodiment, the matrix is a polyacrylamide matrix, wherein the first diameter is greater than the second diameter, and wherein the first temperature range is below the second temperature range. In a more preferred aspect of this embodiment, the first temperature range is between 0° C. and 31° C. and the second temperature range is from 31° C. to 60° C. In a most preferred aspect of this embodiment, the thermoresponsive microparticles are PNIPAM particles. Preferably, the thermoresponsive microparticles represent between greater than zero and 40% of the hydrogel by weight. More preferably, the thermoresponsive microparticles represent between greater than zero and 10% of the hydrogel by weight. Most preferably, the thermoresponsive microparticles represent between greater than zero and 4% of the hydrogel by weight. Preferably, N,N'-methylene-bis-acrylamide (Bis) represents between greater than zero and 10% of the hydrogel by weight. More preferably, Bis represents between greater than zero and 6% of the hydrogel by weight. Most preferably, Bis represents between 2% and 6% of the hydrogel by weight.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

FIG. 1A shows the idealized matrix geometry; FIG. 1B depicts hydrodynamic transport along fluid streamlines (broken lines); and FIG. 1C shows electrophoretic transport along a homogeneous electrical field (broken lines).

2, where $R_s$=1.5, a reasonable degree of separation is achieved. None of these panels illustrate the optimal separation $R_s$=2.0 in which complete separation would be achieved.

Figure 3A:
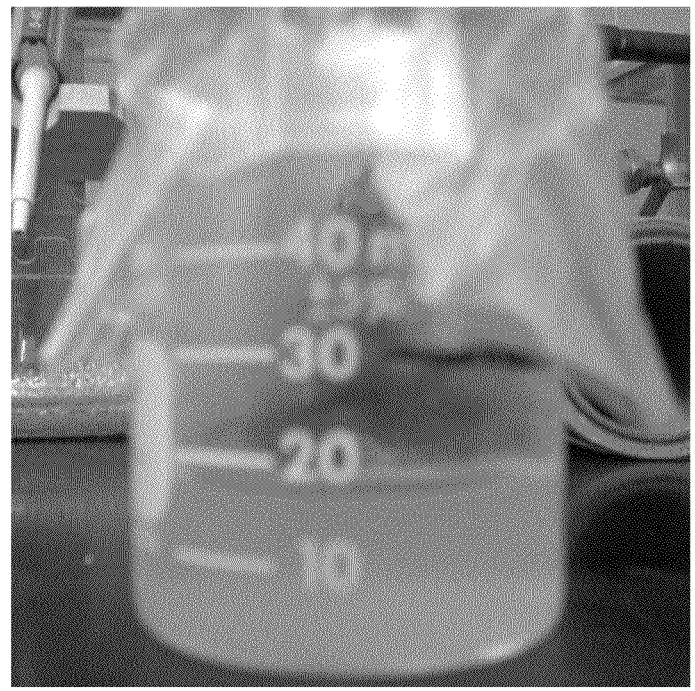
Figure 3B:
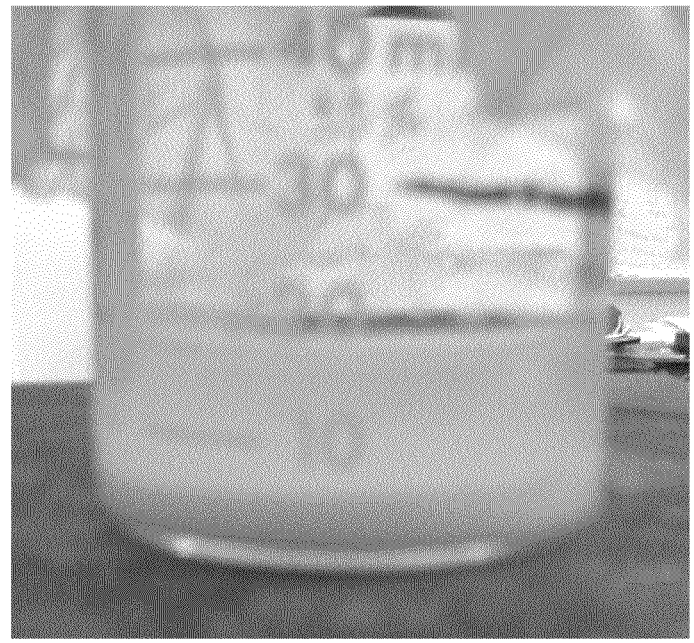

FIG. 3A shows pristine microparticles at 32° C., and FIG. 3B shows the same mixture at 37° C. Note the precipitate visible at the higher temperature.

Figure 4A:
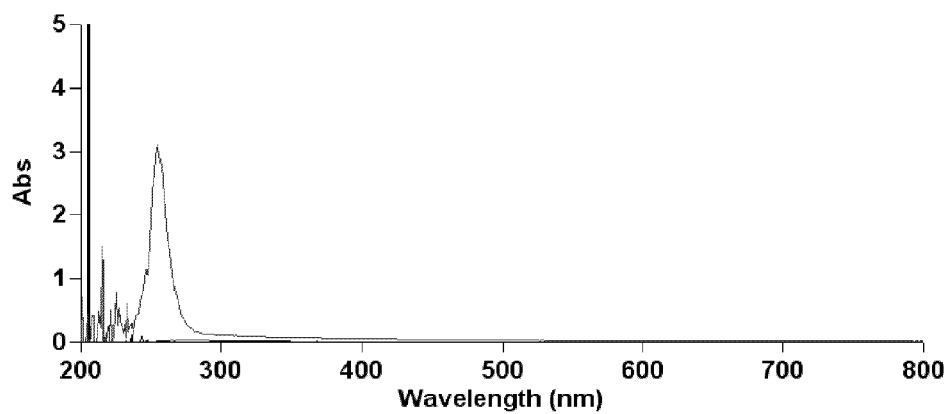
Figure 4B:
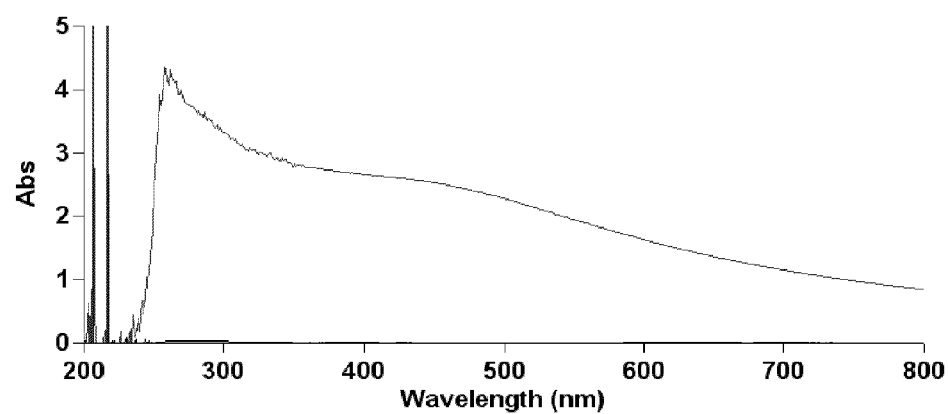
Figure 4C:
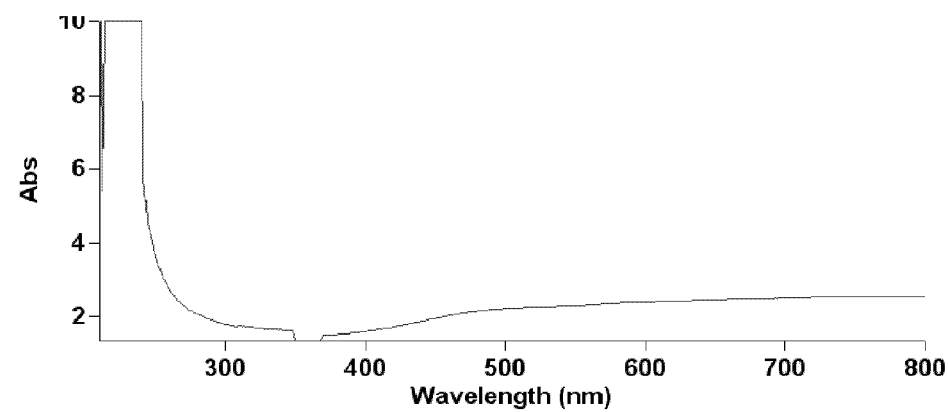

FIGS 4A-C show UV/Vis scans. FIG. 4A is a UV/Vis scan of NIPAM monomer; FIG. 4B is a UV/Vis scan of PNIPAM microparticles at room temperature; and FIG. 4C is a UV/Vis scan of supernant fluid collected from precipitation at 38° C.

Figure 5:
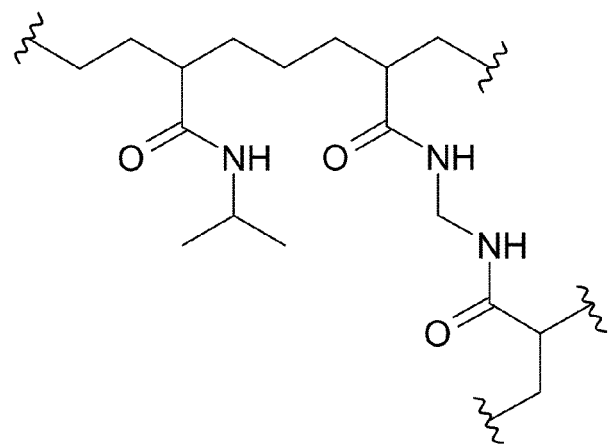

FIG. 5 shows a schematic of the chemical structure of the PNIPAM microparticles, and depicts schematically a molecule of PNIPAM in complex with a molecule of N,N'-methylene-bis-acrylamide.

Figure 6:
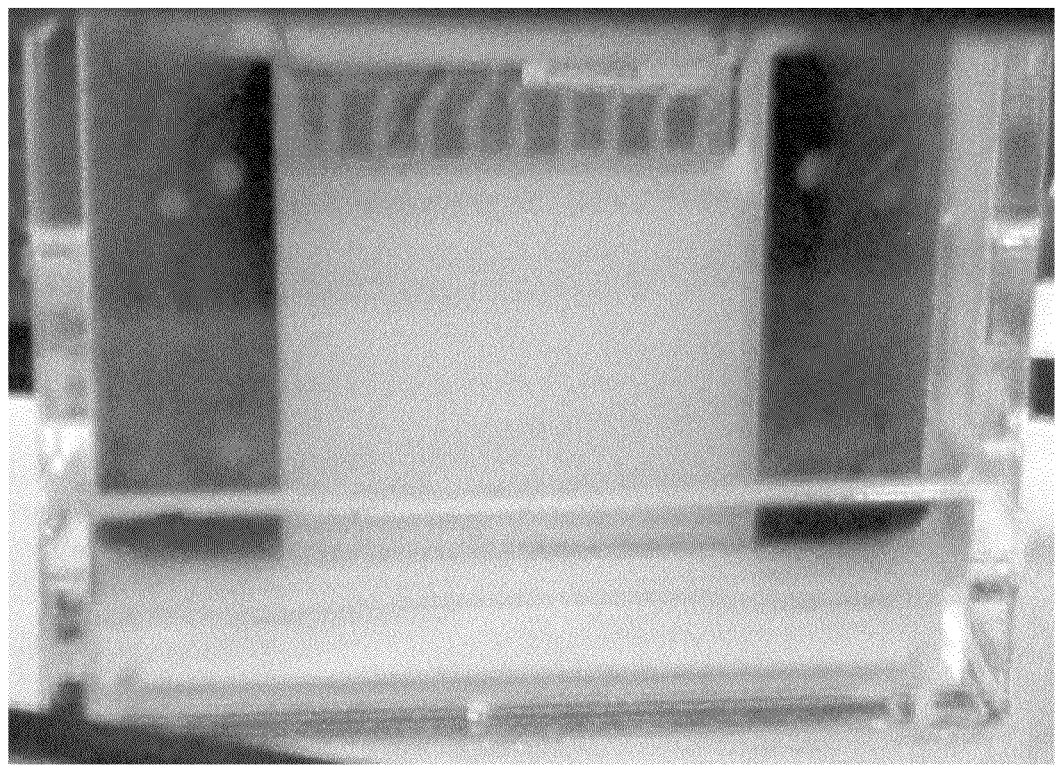

FIG. 6 shows a vertical electrophoresis casting setup.

Figure 7:
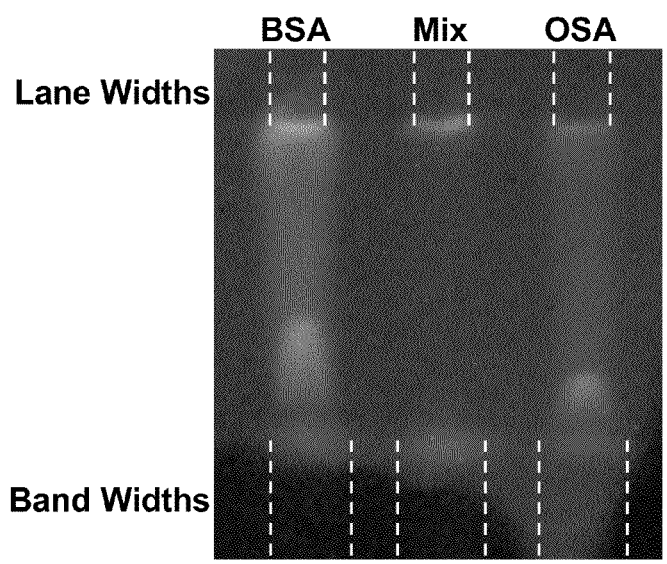

FIG. 7 shows electrophoresis results for OSA in a polyacrylamide control gel (no PNIPAM microparticles) at 26° C. Note that the band has not remained in discrete lanes, indicating that band dispersion is high.

Figure 8A:
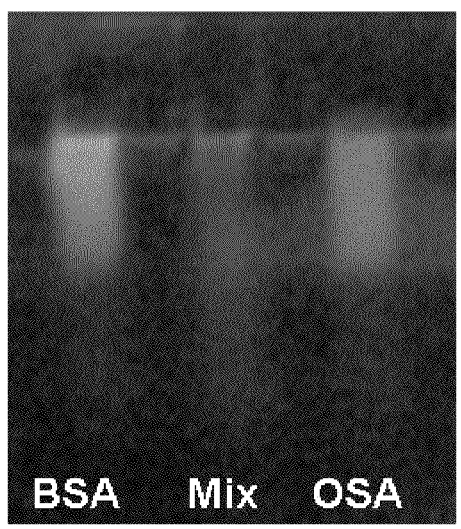
Figure 8B:
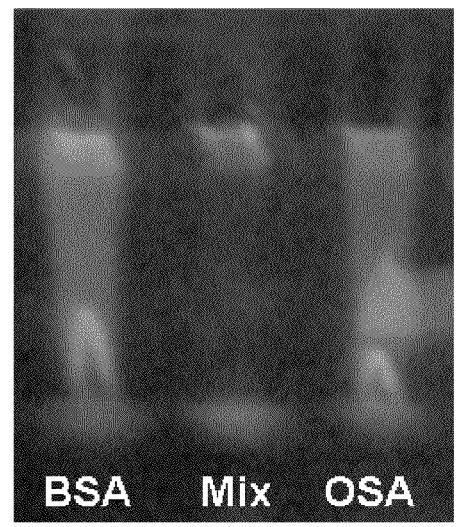

FIGS. 8A and 8B show band separation after gel electrophoresis performed at 26° C. with OSA, BSA, and an equal volume mixture of OSA and BSA ("Mix"). FIG. 8A shows a control gel, and FIG. 8B shows a composite gel containing PNIPAM microparticles.

Figure 9A:
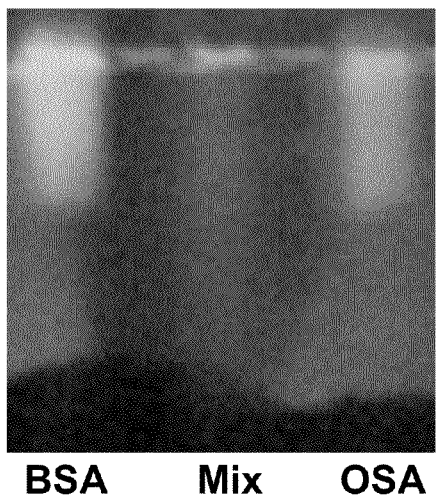
Figure 9B:
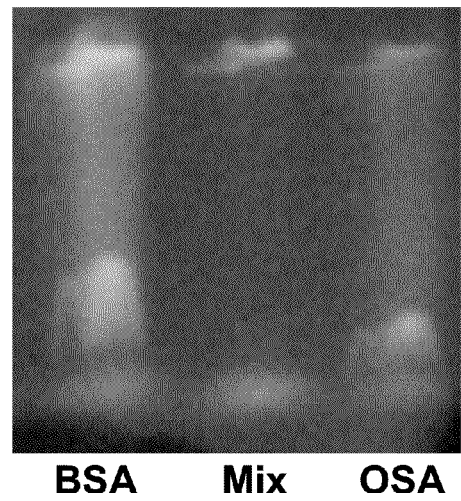

FIGS. 9A and 9B show the results of high-temperature (34° C.) electrophoresis of BSA, OSA, and an equal volume mixture of OSA and BSA ("Mix"). FIG. 9A shows a control gel with no PNIPAM microparticles. The three lanes from left to right are BSA, OSA+BSA ("Mix"), and OSA. FIG. 9B shows a gel composite with PNIPAM microparticles and voids. The lane order for FIG. 9B is the same as in FIG. 9A. For practical reasons, the gels in FIGS. 9A and 9B were returned to room temperature (26° C.) for 1-2 minutes prior to imaging—the protein bands are not visible under UV light in opaque, high temperature composite gels.

Figure 10A:
Figure 10B:

FIGS. 10A and 10B show a comparison of composite gel opacity at 26° C. (FIG. 10A) and 34° C. (FIG. 10B). In FIG. 10B the PNIPAM microparticles have passed through the LCST and their volume has decreased, leaving microvoids in the polyacrylamide matrix gel.

DETAILED DESCRIPTION OF THE INVENTION

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

As is generally the case in biotechnology and chemistry, description of the present invention requires the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which the methods described herein belong. Definitions for other terms also appear elsewhere herein. However, the definitions provided here and elsewhere herein should always be considered in determining the intended scope and meaning of the defined terms. Other than in the operating examples or where otherwise indicated, all numbers or expressions referring to quantities of ingredients, reaction conditions, etcetera, used in the specification and claims are to be understood as modified in all instances by the term "about."

A "hydrogel" is a material consisting of a crosslinked polymer matrix that is swollen in water. Hydrogels are often used to separate biomolecules (e.g., proteins and/or nucleic acids) via pores in the gel structure. When used for applications involving separations, the polymer matrix is often based on either agrose or acrylamide monomers. However, composites or gels with multiple phases, beyond just the water and the primary polymer, can be produced by adding micro- or nanoparticles. Even low concentrations of these added particles give the gel distinct morphologies that can result in a very different ability to resolve mixtures of biomolecules. In addition, the mechanical properties of these materials show quite different characteristics that may aid in increasing options for gel handling (see, e.g., O. Okay and W. Opperman, "Polyacrylamide-clay nanocomposite hydrogels: Theological and light scattering characterization," Macromolecules. 2007; 40:3378-3387, hereby incorporated by reference in its entirety).

The porous morphology of hydrogels produces variation in the migration of macromolecules within the hydrogel. Because molecules of different size, shape, and charge move at different rates through a hydrogel, they become separated over time and in an ideal situation they become isolated from one another. The pore size distribution of gel morphologies can be controlled experimentally through parameters such as polymer matrix composition, solvent factors, and crosslink density. Control of the intrinsic pore size distribution is a critical issue, and will be discussed in greater detail below. As mentioned above the pores act as molecular sieves or size-exclusion filters when biomolecules move through the gel. The pore size distribution can determine how macromolecules move or "transport" through the matrix. Surfactants such as sodium dodecyl sulfate (SDS) have traditionally been used in hydrogel-based separations media. The role of the surfactant in electrophoresis may vary, but in some cases it can be used to alter the pore size distribution (see, e.g., J. M. Berg, J. L. Tymoczko, and L. Stryer, Biochemistry, 6th ed. ed. New York: W. H. Freeman and Company, 2007; and J. A. Pascal, H. A. Stretz, M. A. Oyanader, and P. E. Arce, "Electrohydrodynamics in nanoparticle embedded gels: effects of morphology and electrostatic potential," presented at AIChE National Conference Proceedings, Salt Lake City, Utah, 2007, each of which is hereby incorporated by reference in its entirety).

"Electrophoresis" is the motion of dispersed particles relative to a fluid under the influence of an electric field that is uniform in space; it also refers to the electromotive force used to move molecules through a gel matrix. In gel electrophoresis, an electrical field is applied to a gel, and it provides the primary driving force for transport and separation of biomolecules within the gel. The field can either be parallel or orthogonal to the macromolecule within the gel (see, e.g., Ma X, Sauer J. A., Hara M. "Poly(methy1 methacrylate) Based Ionomers. 1. DynamicMechanical Properties and Morphology." Macromolecules 1995, 28, 3953-3962, hereby incorporated by reference in its entirety). Since proteins are charged particles, they are sensitive to the electrostatic force exerted by the electrical field. By placing the molecules in wells in the gel and applying an electric current, the molecules will move through the matrix at different rates as a function of their size (mass), shape, and charge and so become separate from one another. As earlier mentioned, these properties lead to two important macroscale quantities, the electrophoretic mobility and the effective diffusivity. By adjusting the electric field characteristics and gel morphology, one can successfully separate macromolecules in a given mixture.

When separating bio-macromolecules ("biomolecules") in a gel, their separation should be detected and measured in some fashion. As used herein, "biomolecules" refers to biologically-derived or biologically-related molecules including, but not limited to, nucleic acids (e.g., strands of RNA, DNA, etc.) and proteins, and includes DNA, RNA, or protein sequences with naturally-occurring nucleic or amino acids as well as those with synthetic or artificial nucleic or amino acids. The transport or movement of the biomolecules can be detected visually by labeling the macromolecule with either a fluorescent stain such as dansyl chloride or a visible stain such as Coomassie brilliant blue (see, e.g., Berg, 2007; and J. A. Pascal, R. O'Hara, M. A. Oyanader, and P. E. Arce, "Optimal separation times for electrical field flow fractionation with couette flows," Electrophoresis, 2008:29; 1-9, hereby incorporated by reference in its entirety), thus rendering them detectable (e.g., visually, photographically, digitally, etc.). Other stains, including Ethidium Bromide or silver may be used, and the molecules separated may also incorporate a radioactive label (which may be detected via autoradiography). If a fluorescent stain (a "fluorochrome") is chosen, a particular wavelength of UV light (excitation wavelength, or "Ex") is used to excite the fluorophore (the component of the fluorochrome responsible for fluorescence), which absorbs that light and emits light at a different and characteristic wavelength (emission wavelength, or "Em"), often in the visual range. For example, and without intending to be limited, the fluorochrome may be attached covalently to the biomolecules within the gel before electrophoresis, or it may be attached to an antibody, the antibody being used to detect the separated biomolecules. In practice, one exposes the entire gel to light of a wavelength appropriate for the fluorochrome used. In response, the biomolecule bands (covalently attached to or otherwise associated with fluorochrome) within the gel emit visible light, and their positions are recorded (e.g., photographically). One difficulty of labeling biomarkers is that the chemical reaction with the fluorochrome may alter the biomarker's structure, and this structural change must be accounted for in any models based on fluid dynamics or electrokinetics. The flows were normalized by dividing distance traveled in the composite gels versus distance traveled in the control gels (see, e.g., TABLE 5).

The electrophoretic mobility and the effective mobility depend upon several different properties. Some of these include: material composition, macromolecules to be separated, and electric field properties. These field properties include pH (where $pH=-\log_{10}[H^+]$, where "$[H^+]$" is the hydrogen ion concentration), molecular charge, size of the molecule and its shape, electric field strength, and molecule orientation, among others. In addition, the charge of a given protein (or DNA) depends on the pH of the solvent used. Each of the monomers making up the protein will contain interactive amide, acid, or thiol groups and each of these offer a different acid dissociation constant (or "$pK_a$," where $pK_a=-\log_{10} K_a$) for protonation. Thus, all electrophoresis of proteins (for example, and without limitation) is conducted in a buffer solution which determines pH. Therefore, separations run for the same two biomolecules using buffers with differing pH values may produce different results because the charge (and even the three-dimensional shape) of each protein may vary along with pH. Thus, in order to produce a meaningful comparison, the conditions for the new nanocomposite PNIPAM gels and the control or "regular" gels must be chosen carefully (see, e.g., EXAMPLES 1 and 2).

Figure 2:
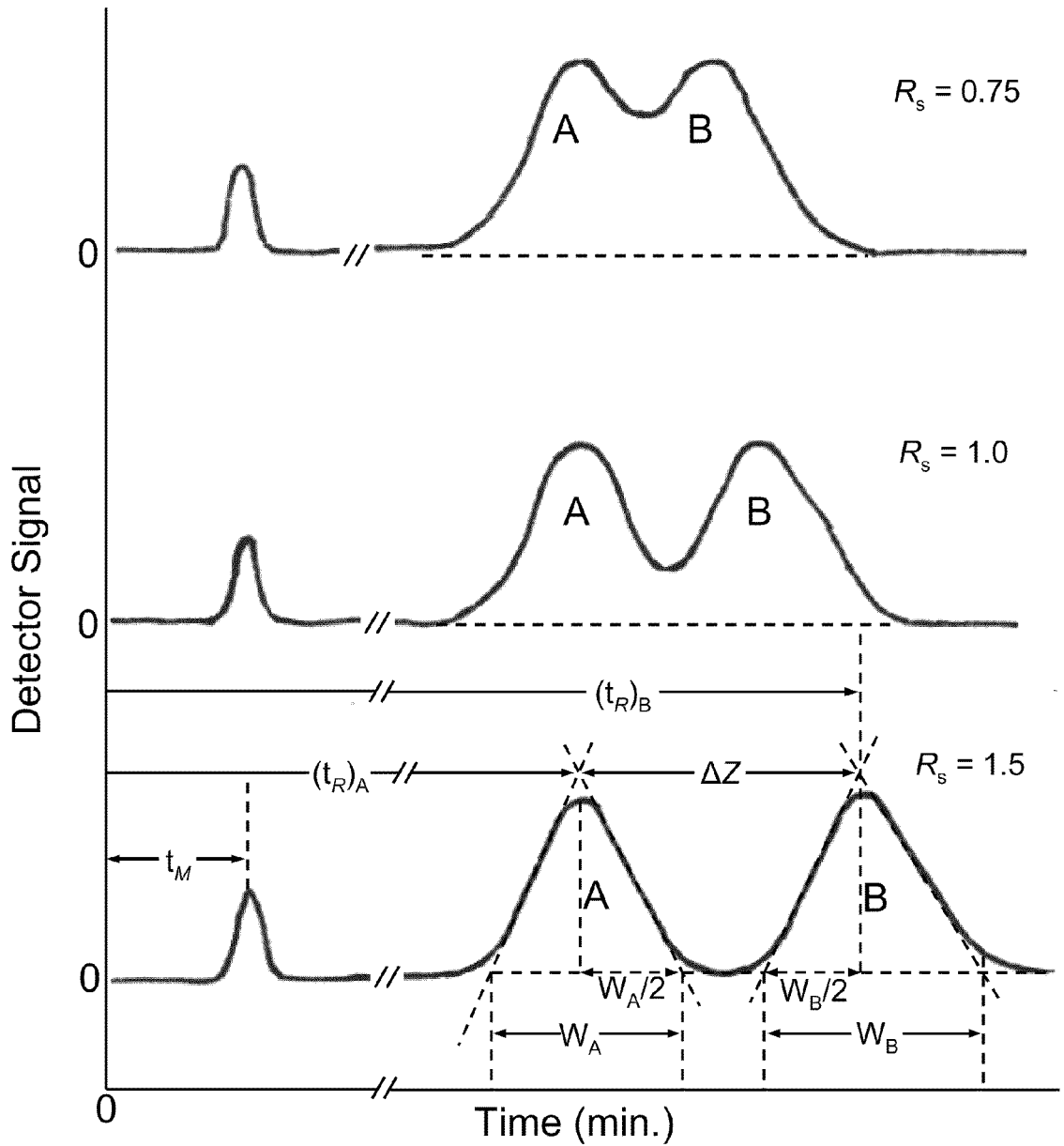
FIG. 2 illustrates the various types of separation as described in Skoog and Leary. In the top panel of FIG. 2, where $R_s<1.0$, no separation is achieved. In the middle panel of FIG. 2, where $R_s=1.0$, some degree of separation is achieved, but not an optimal one. In the bottom panel of FIG.

The separation of two biomolecules (initially well mixed) is characterized visually by measuring band resolution after electrophoresis. The resolution of the two bands can be described as one of three distinct types (see, e.g., Skoog, D. A.; Leary, J. J., An Introduction to Chromatographic Separations. In Principles of Instrumental Analysis, Harcourt Brace College Publishers: New York, 1992; 4th ed, 579-604, hereby incorporated by reference in its entirety). As seen in FIG. 2, the best resolution ($R_s$>1.5) is characterized by two distinct bands with a space between them. A second and acceptable level of resolution ($R_s$>1.0) is characterized by two bands which, while not well-defined, overlap only to an insignificant extent. For a poor separation, i.e. poor resolution ($R_s$<1.0), the operator will observe bands which are overlapping (i.e., movement of the biomolecule mixture through the gel does not result in clearly separated bands). A figurative diagram of these three general types of resolution is shown in FIG. 2, as described by Skoog and Leary, 1992. A resolution of $R_s$=2 (not shown) is considered optimal resolution in gel electrophoresis. Under these conditions, an optimal time of separation ("$\tau_{op}$") has been defined to be as shown in Formula 1, where "$D_{eff\,A}$" and "$D_{eff\,B}$" are the effective global diffusivity of components A and B, respectively, $D_A$ and $D_B$ are the diffusion coefficients for components A and B, respectively, and $\hat{V}_{eff\,A}$ and $\hat{V}_{eff\,B}$ are the effective convective velocities of components A and B, respectively (see, e.g., Pascal, AIChE National Conference Proceedings, 2007; and Pascal et al., 2008, each of which is hereby incorporated by reference in its entirety):

$$\tau_{op} = \left[\frac{\sqrt{D_{eff\,A}/D_A} + \sqrt{D_{eff\,B}/D_B}}{\hat{V}_{eff\,A} - \hat{V}_{eff\,B}}\right]^2 \quad \text{Formula 1}$$

Poly-(N-isopropyl acrylamide) ("PNIPAM") is a polymer that exhibits thermoresponsive behavior at temperatures between 31 and 34° C. At or above this temperature range, PNIPAM polymer shrinks, while below this range it swells. As shown in EXAMPLE 3 below, the phenomenon is reversible when the polymer is reacted into a crosslinked polyacrylamide matrix.

PNIPAM solutions in water have been studied extensively due to their ability to undergo thermodynamic phase changes at temperatures (31° C. to 34° C.) very close to room temperature (about 25° C. to 26° C.) (see, e.g., A. St. John, V. Breedveld, and A. L. Lyon, "Phase behavior in highly concentrated assemblies of microgels with soft repulsive interaction potentials," Journal of Physical Chemistry B, 2007; J. G. McGrath, R. D. Bock, M. Cathcart, and A. L. Lyon, "Self-assembly of "paint-on" colloidal crystals using poly(styrene-co-N-ispropylacrylamide, each of which is hereby incorporated by reference in its entirety) spheres," Chemistry of Materials, vol. 19, pp. 1584-1591, 2007; D. Suzuki, J. G. McGrath, H. Kawaguchi, and A. L. Lyon, "Colloidal crystals of thermosensitive core/shell hybrid microgels," Journal of Physical Chemistry C, vol. 111, pp. 5667-5672, 2007; S. Nayak, D. Gan, M. J. Serpe, and A. L. Lyon, "Hollow thermorsponsive microgels," Small, vol. 1, pp. 416-421, 2005; C. M. Nolan, C. D. Reyes, J. D. Debord, A. J. Garcia, and A. L. Lyon, "Phase transition behavior, protein adsorption and cell adhesion resistance of poly(ethylene glycol) cross-linked microgel particles," Biomacromolecules, vol. 6, pp. 2032-

2039, 2005; N. Ishida and S. Biggs, "Direct observation of the phase transition for a poly(N-isopropylacrylamide) layer grafted onto a solid surface by AFM and QCM-D," Langmuir, vol. 23, pp. 11083-11088, 2007; and K. N. Plunkett, X. Zhu, J. S. Moore, and D. E. Leckband, "PHIPAM chain collapse depends on the molecular weight and grafting density," Langmuir, vol. 22, pp. 4259-4266, 2006, each of which is hereby incorporated by reference in its entirety). As can be seen in FIG. 3, at temperatures above the phase change temperature the PNIPAM microparticles become hydrophobic, desolvate, and collapse within themselves. This is an example of a lower critical solution temperature (LCST)—a phase change in which demixing occurs as the solution temperature is raised. This is a system temperature that is readily accessible under biological conditions.

The PNIPAM phase transition has been visualized using atomic force microscopy by Ishida and Biggs, 2007, apparently under tapping mode. By varying the modulus of elasticity at various temperatures, it is possible to visualize differences in the hardness of the materials. This work suggests that the volume phase transition occurs somewhere between 31° C. and 33° C., and the particles become rigid beyond the LCST (above 31° C. to 33° C.) due their collapse in water. The authors discuss a brush-to-mushroom type transition of the conformation of the polymeric particles. According to these results the most abrupt change is visualized at the phase transition with other more subtle changes as the temperature continues to increase. In addition, research has shown that the chain collapse characteristics depend on the molecular weight of the particles. In recent findings, PNIPAM was found to have highly pronounced volume phase transitions at higher molecular weights above approximately 200,000 a.u. (see, e.g., Plunkett, 2006).

Figure 1A:
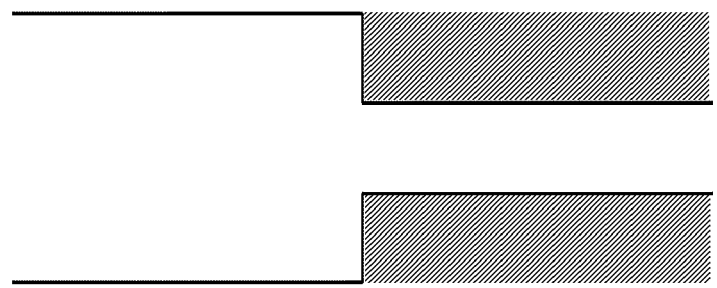
FIGS. 1A, 1B, and 1C show idealized geometry for a matrix whose pore sizes exhibit a bimodal distribution (a narrow channel and a wide channel) (Trinh et al., 1999).
Figure 1B:
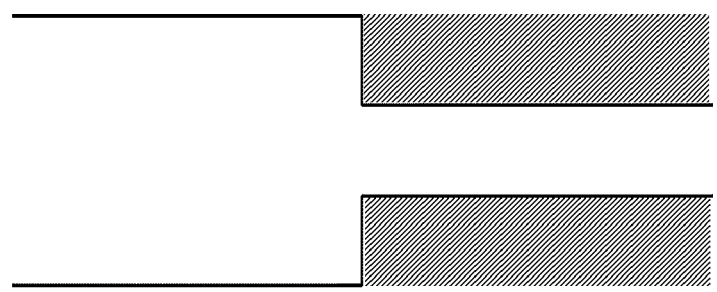
Figure 1C:
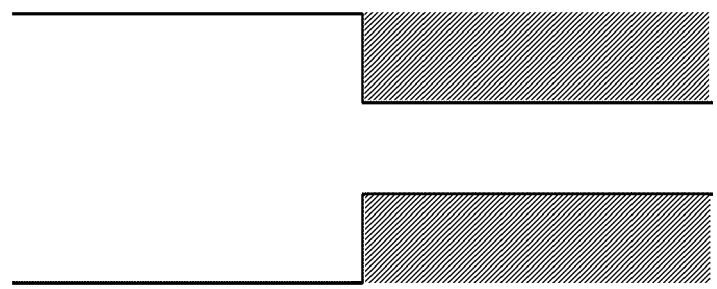

Since PNIPAM is not a living polymer, it has a distribution of molecular weights. This distribution can be measured using dynamic light scattering techniques (DLS). Dynamic light scattering was performed on particles synthesized in the same fashion as those of the present invention (see, e.g., St. John, 2007, hereby incorporated by reference in its entirety). The hydrodynamic radius of such particles varied between 100 nm and 500 nm (see, e.g., FIGS. 1A, 1B, and 1C). In addition, St. John also reported that the free volume of the particle can be a function of how well the particles can be compressed. Thus, PNIPAM particles—on the order of a few hundred nanometers—could create "macrovoids" within a polymer matrix.

PNIPAM is also used in copolymer formulations for studying novel methods of drug delivery, usually wherein each PNIPAM molecule is grafted (linked) to another molecule (e.g., polyethyleneimine). These grafted structures have also been studied for their thermodynamic and mechanical properties.

PNIPAM has also been copolymerized with polystyrene (see McGrath, 2007, suggesting that the copolymer does not exhibit thermoresponsiveness at low concentrations of PNIPAM in a non-aqueous media). In an aqueous media, the particles were found to shrink as much as 61.4% by volume for lower concentrations of PNIPAM for the same temperatures in non-aqueous media. This suggests that the microparticles will aggregate during any solvent-driven drying process.

Copolymerization of PNIPAM has been observed with polyethylene glycol, or "PEG" (see Nolan, 2005). In this study, PEG chain grafting length was found to play a role in the thermoresponsive behavior of the composite. The phase transition temperature increased as PEG chain length increased, and this phenomenon was also true for composites of low molar cross-linking concentrations.

Finally, PNIPAM has been used to create a "gated" composite (see C. Yang, D. Li, and J. Masliyah, "Modeling forced liquid convection in rectangular microchannels with electrokinetic effects," International Journal of Heat and Mass Transfer, vol. 41, pp. 4229-4249, 1998, hereby incorporated by reference in its entirety). These gated composites were formed using polycaprolactam ("nylon 6") as well as polyvinylidene fluoride ("PVDF"), with nylon 6 existing as the skeleton. With temperature held constant, PNIPAM appeared to lessen the amount of material that was able to enter and exit nylon 6. This suggests a gating effect that offers potential use in pharmaceutical drug delivery applications. Thus, future work with PNIPAM particles could easily feature grafted technologies, and the foregoing speaks to the flexibility of the composite PNIPAM microparticle-and-polyacrylamide composite approach (e.g., a variety of microparticles could be synthesized to vary the effects of microparticle morphology, sizes, and shape on composite properties).

All of the polyacrylamide gels discussed herein were synthesized by methods laid out by Tanaka (see T. Tanaka, From Gels to Life. Tokyo: University of Tokyo Press, 2002; and T. Tanaka, "Gels," Scientific American, vol. 244, pp. 124-136, 1981, hereby incorporated by reference in its entirety), which is hereby incorporated by reference in its entirety. The pore size inherent in a crosslinked polymer structure is a function of the crosslink density as well as the amount and type of solvent that swells the matrix. Two equations (Formulas 2 and 3) are used to help specify the composition of a swollen hydrogel, where "% T" is the mass polymer/volume water and "% C" is the mass fraction of the crosslinker in the polymer (see, e.g., Ugaz and Wang, 2006).

$$\% \ T = \frac{mass_{monomer} + mass_{crosslinker}}{Volume_{solution}}; \quad \text{units } \frac{g}{ml} \quad \text{Formula 2}$$

$$\% \ C = \frac{mass_{crosslinker}}{mass_{monomer} + mass_{crosslinker}}; \quad \text{units } \frac{g}{g} \quad \text{Formula 3}$$

Several methods have been used to characterize the resulting pore size and pore size distribution. TABLE 1 presents data estimated from distributions given by Wang and Ugaz, 2006, where % T and % C were varied and pore sizes measured by thermoporometry (a method that depends on a distribution of freezing temperatures for ice in confined spaces using dynamic scanning calorimetry (see, e.g., Skoog, 1992)). Unlike the gels of the present invention, which used thermal crosslinking techniques, the polyacrylamide samples represented in TABLE 1 were crosslinked using photopolymerization techniques. Nevertheless, the data provide some idea of the range of pore sizes to expect.

TABLE 1

| | Average Pore Size (nm) | | |
| --- | --- | --- | --- |
| | % T (g/ml) | | |
| % C (g/g) | 6 | 9 | 12 |
| 1 | | 9.3 | |
| 3 | | 8.6 | |
| 5 | 12.7 | 8.3 | 6.7 |
| 7 | | 7.5 | |
| 9 | | 7.5 | |

Recall that the protein probes used herein (e.g., ovine serum albumin and bovine serum albumin) are about 3 nm to 8 nm in diameter (see J. J. Brownsey, T. R. Noel, R. Parker, and S. G. Ring, "The glass transition behavior of the globular protein bovine serum albumin," Biophysical Journal, vol. 85, pp. 3943-3950, 2003, hereby incorporated by reference in its entirety), the range representing anisotropy of the molecule, which is not in any case a perfectly rigid prism. In contrast, the templated pores, or "voids" (i.e., the voids left behind and bounded by the polyacrylamide matrix when the PNIPAM particles held inside the polyacrylamide matrix shrink during a temperature change) are on the order of 200 nm.

EXAMPLE 1

PNIPAM Microparticle Synthesis

This EXAMPLE 1 will discuss the synthetic scheme for cross-linked poly(N-isopropyl acrylamide) microparticles (see TABLE 2 for reactant information). The %/C, as described by Formula 3, is expected to be 1.7% for a complete reaction. % C could be described as the mass fraction of crosslinker in the reaction matrix. This method of synthesis is described in St. John et al., 2007, which reference is hereby incorporated in its entirety. All reagents were used as received from their respective sources. The reactants were agitated by magnetic stirrer for at least one hour to achieve thorough mixing. Mixing was judged complete when all particulates appeared to be in solution. The resulting solution was degassed using a nitrogen purge for one hour. The solution container was then immersed in a 70.0° C. constant temperature bath, flushed with nitrogen, and the initiator was stirred in for 4 hours. Upon reaction completion, a precipitate formed at the bottom of the flask. The precipitate was then cooled to 4.0° C. for 24 hours, at which temperature the particles re-solvated in the water and the solution was highly viscous and turbid. Fully solvated particles in water are expected to be about 400-800 nm in diameter as reported by St. John et. al., 2007.

TABLE 2

Reactants for Microparticle Synthesis

| Material | Amount | Source |
| --- | --- | --- |
| N-isopropyl acrylamide (NIPAM) | 1.5690 g | Fisher Scientific |
| Distilled/Deionized water | 100.0 mL | Purified in house |
| N,N'-Methylene-bis-acrylamide (BIS) | 0.0277 g | Fisher Scientific |
| Ammonium Persulfate | 0.0346 g | Fisher Scientific |
| % $T_{part}$ | 1.6% | — |
| % $C_{part}$ | 1.7% | — |

EXAMPLE 2

PNIPAM Microparticle Characterization

Particles synthesized according to the methods of EXAMPLE 1 were characterized by two primary methods: visual observation of the lower critical solution temperature transition ("LCST"); and UV/Vis spectra taken above and below the transition. The water/PNIPAM particle mixture was photographed at a temperature below the LCST (32° C.) (see FIG. 3A), and then subsequently above the LCST (34° C.) (see FIG. 3B). The precipitation of particles noted in these images above the LCST is one indicator of the quality of the particles produced (i.e., below a critical molecular weight there would have been no observable transition), and suggests that the particles synthesized according to the methods of EXAMPLE 1 were of suitable quality.

A Varian UV/Vis spectrophotometer equipped with Cary Win UV software (Varian, Inc., Palo Alto, Calif.) was used to obtain spectra of the PNIPAM microparticles, using a scanning range between 200 and 800 nm (see FIGS. 4A-4C). FIG. 4A shows the UV/Vis spectrum of NIPAM monomer; FIG. 4B shows the UV/Vis spectrum of PNIPAM microparticles at room temperature (26° C.); and FIG. 4C shows the UV/Vis spectrum of supernatant fluid collected from PNIPAM particles subjected to elevated temperature (38° C.). To review the types of absorbances that might be expected in this range, one characteristic or signature absorbance would be related to the crystal spacing of a precipitated/dispersed set of nanoparticles. It has been established that the UV/Vis absorption of microgel dispersions can be related to Bragg diffraction from ordered arrays or aggregates of particles, often termed "inverse opals." Here, the lattice spacing for these ordered particles is on the order of the wavelength of light. As the temperature of the solution decreases, the wavelength of the peak would not change significantly, but intensity will be reduced if the ordered arrays were dispersed through salvation (see G. Huang and Z. Hu, "Phase behavior and stabilization of microgel arrays," Macromolecules, vol. 40, pp. 3749-3756, 2007, hereby incorporated by reference in its entirety). The turbidity of the microgels has also been found to be dominated by the amount of water in the interstitial region (see Q.-S. Zhang, L.-S. Zha, J.-H. Ma, and B.-R. Liang, "Synthesis and characterization of novel, temperature-sensitive microgels based on N-isopropylacrylamide and tert-butyl acrylate," Journal of Applied Polymer Science, vol. 103, pp. 2962-2967, 2007, hereby incorporated by reference in its entirety). For the spectroscopic results shown in FIGS. 4A-4C, these opalescent particle aggregatees were not noted, partly because FIG. 4C shows the UV/Vis spectrum of the supernant fluid, not the precipitate, at the higher temperature. Visually, however, at least one of the samples did show a visual pink tinge after synthesis, and the inventors regarded this as evidence of the opalescent array of particles. FIGS. 4A and 4B exhibit the absorbance at room temperature of NIPAM monomer and PNIPAM, respectively. PNIPAM shows a new absorbance pattern over NIPAM monomer, indicating a structural change. In FIG. 4C, however, the supernatant fluid from the higher-temperature precipitation of PNIPAM still shows evidence of the NIPAM monomer (compare to FIG. 4A). Clearly, polymerization is not complete at the higher temperature, but the evidence of a precipitate and the broad absorbtion in FIG. 4B does indicate that some particles were produced, albeit the final solution is not completely purified of excess monomer. A schematic of the chemical structure of the PNIPAM microparticles is given in FIG. 5.

EXAMPLE 3

Control Gel and PNIPAM Composite Gel Synthesis

Composite composition is often described using the parts per hundred resin (pphr) technique as a basis, because many composites contain three or more phases (e.g. resin, fiberglass, sizing). Often when working with three phases, one wishes to keep the ratio between two of the phases the same while varying the third component. Thus, it is easier to communicate to an audience what is being varied if two of the components add up to 100% and the third component is considered to be composition beyond 100%. This technique is adopted here, and it is assumed that the concentration of the gel matrix (the acrylamide resin and its crosslinkers together) forms the basis for the "resin." PNIPAM microparticles, even though they are polymer resin in nature, are described as the filler (third component), and therefore some percentage over 100%. The % T and % C calculations in this EXAMPLE 3 are calculated to describe monomer reacted to become gel matrix, and will not include monomer polymerized to produce the PNIPAM microparticles. To differentiate the two calculations, the PNIPAM microparticle values will hereafter be referred to as % $T_{part}$ and % $C_{part}$, and the gel matrix values will be referred to as % $T_{matrix}$ and % $C_{matrix}$. To recap Formulas 2 and 3, % T is the mass polymer/volume water, and % C is the mass fraction of the crosslinker in the polymer. Two varieties of gels were synthesized: a control poly-acrylamide gel; and a micro-gel composite comprising PNIPAM-co-polyacrylamide ("PNIPAM-co-PA"). Synthesis of the control polyacrylamide gel is discussed first.

Control gels consisting solely of poly-acrylamide crosslinked with bis-acrylamide (N,N'-methylene-bis-acrylamide) were prepared according to the reaction scheme in TABLE 3. The parameters for these gels are % $T_{matrix}$=4.8 and % $C_{matrix}$=3.1. For each, the mixture was agitated for one hour to achieve thorough mixing, as determined by visual inspection. To initiate polymerization, 10 mL of the mixture was combined with 50.0 µL of ammonium persulfate (APS), a radical producing agent, and 5.0 µL of N,N,N',N'-Tetramethylethylenediamine (TEMED), a chemical initiator. The mixture containing APS and TEMED was quickly poured into a gel casting setup (see, e.g., FIG. 6), and a comb was fitted into the top and between the plates to produce wells. Gel production takes approximately 1.0 hours after chemical initiation with TEMED.

TABLE 3

Reactants for Control Polyacrylamide Gel

| Reagent | Amount | Source |
| --- | --- | --- |
| Acrylamide | 1.10604 g | Fisher Scientific |
| Bis-Acrylamide | 0.0356 g | Fisher Scientific |
| Distilled/Deionized Water | 23.5 mL | In House |
| % $T_{matrix}$ | 4.8 | |
| % $C_{matrix}$ | 3.1 | |
| % Filler Particles (w/w) | 0 | |

Composite gels were prepared according to the reaction scheme of TABLE 4. The % $T_{matrix}$ and % $C_{matrix}$ for these gels are 4.7 and 3.2, respectively. For each, the mixture was agitated for 25.0 hours to ensure sufficient mixing. Judging the thoroughness of mixing by visual inspection is not possible for the composite gels because the solution still appears turbid even after mixing for well beyond 100 hours. After 25.0 hours, the turbidity of the solution is uniform, and this uniformity is used to judge that mixing is complete. Importantly, these composite gels are created at ambient temperature (approximately 26° C.)—which is below the phase transition temperature for PNIPAM in water—and thus the microparticles are soluble. To initiate polymerization, 10 mL of the mixture was combined with 50.0 µL APS and 5.0 µL TEMED. The mixture containing APS and TEMED was quickly poured into a gel casting setup (see, e.g., FIG. 6), and a comb was fitted into the top and between the plates to produce wells. Composite gel polymerization ("gelation") takes approximately 1.0 hours after chemical initiation with APS and TEMED.

TABLE 4

Reactants for Composite Gel

| Reagent | Amount | Source |
| --- | --- | --- |
| Acrylamide | 1.5007 g | Fisher Scientific |
| Bis-Acrylamide | 0.05001 g | Fisher Scientific |
| Distilled/Deionized Water | 23.5 mL | In house |
| PNIPAM solution | 9.437 g | In house reaction |
| % $T_{matrix}$ | 4.7 | — |
| % $C_{matrix}$ | 3.2 | — |
| % Filler particles (w/w) (no water) | 9.7 | — |

After one hour, the wells were covered with water to prevent them from drying out. All gels were then refrigerated for at least 24 hours at 4° C., and were then characterized by visual inspection and gel electrophoresis. Preferably, the microparticles represent between greater than zero and 40% of the composite gel by weight. More preferably, the microparticles represent between greater than zero and 10% of the composite gel by weight. Most preferably, the microparticles represent between greater than zero and 4% of the composite gel by weight. Preferably, N,N'-methylene-bis-acrylamide (Bis) represents between greater than zero and 10% of the composite gel by weight. More preferably, Bis represents between greater than zero and 6% of the composite gel by weight. Most preferably, Bis represents between 2% and 6% of the composite gel by weight.

EXAMPLE 4

Electrophoresis Results with OSA and BSA Protein Standards

Electrophoresis studies with PNIPAM composite gels were conducted to determine the effect that the matrix has on the mobility of the probes under the influence of an electrical field, including: the typical dispersion of the protein band in a control versus the composite gel; differences, if any, in mobility of each protein along the axis of the field for the control versus the composite gel; differences, if any, in mobility of each protein for the control versus the composite gel after the PNIPAM microparticles undergo a volume change; and whether any of these combinations result in differences in separation for the control versus the composite gel. Here, "separation" means good resolution, and as discussed previously it is a combination of low dispersion and a differential in mobility along the axis of the applied field.

Protein Standards

The two protein probes chosen for this work were ovine serum albumin (OSA, approximately 34 kDa) and bovine serum albumin (BSA, approximately 67 kDa). Because of their different molecular weights, any electrophoretic separation observed should be based upon a sieving effect which is provided by changes in the morphology of the matrix. It is interesting to note that BSA is a dimer whose components are about 32 kDa and 35 kDa (see M. Okubo, I. Azume, and Y. Yamamoto, "Preferential adsorption of BSA dimer onto polymer microspheres having a heterogeneous surface consisting of hydrophobic and hydrophilic parts," Colloid and Polymer Science, vol. 268, pp. 598-603, 1990, hereby incorporated by reference in its entirety), and this fact has an impact on results which will be discussed later. To visualize the protein bands after electrophoresis, a fluorescent label was attached. For this example, the label chosen was dansyl chloride, a dye which emits brilliant yellow fluorescence in the presence of UV light. As will be appreciated by persons having ordinary skill in the art, a variety of labels (including, but not limited to, fluorescent, enzymatic, radioactive, or otherwise) may be useful in this context. Both OSA and BSA stock solutions were labeled with dansyl chloride via sonication (10 mg/ml protein and 1 mg/ml fluorochrome respectively). Dansyl chloride (5-(dimethylamino)naphthalene-1-sulfonyl chloride) is a reagent that reacts with primary amino groups in both aliphatic and aromatic amines to produce stable blue- or green-blue fluorescent sulfonamide adducts. 40 µl of each labeled stock solution was delivered to separate wells (OSA and BSA lanes, respectively—see, e.g., FIGS. 8A and 8B). 25 µL of labeled OSA stock was mixed with 25 µL BSA stock, and 40 µL of the OSA/BSA mixture ("Mix") was applied to a third well (see, e.g., FIGS. 8A and 8B). For both control and composite gels, electrophoresis was performed in a vertically-oriented elecrophoresis rig using 1×TBE Buffer (Tris-Borate-EDTA) at pH=10 and a Fisher FB 1000 gel electrophoresis power supply, providing 50 Volts for 45 minutes. The temperature of the vertical electrophoresis setup was controlled using an integrated heat exchanger and a temperature controller, and the temperature of the bath in contact with the glass plate of the electrophoresis unit was monitored using a mercury thermometer. While the electric field described is parallel to the long axis of the gel, and constant, persons having ordinary skill in the art will appreciate that the electrical field (or fields) may also be orthogonal, and may optionally pulsed (e.g., pulsed field gel electrophoresis).

Results of Band Dispersion in Control Gel at Room Temperature

As shown in FIG. 7, the probes migrated toward the lower part of the gel after electrophoresis, and the distances moved are given in TABLE 5. The band dispersions for further experiments for OSA are also shown in TABLE 5. All dispersions reported in TABLE 5 fall into two general categories: a value between 0.1 and 0.4 cm; or a value labeled "NR." NR means "no resolution," or that the band was so elongated that no upper limit was discernible. For those values which were measurable, it appeared that the composite gel focused the band to a narrower bandwidth in both low temperature (FIGS. 8A and 8B) and high temperature cases (FIGS. 9A and 9B). Clearly, higher running temperature should increase dispersion because particle diffusion scales with $k_B T$ (where $k_B$ is the Boltzmann constant). For the small temperature change in this set of experiments, however, no change in dispersion was noted, as can be seen by comparing the band widths of the two control gels (FIGS. 8A and 9A). However, the morphological change experienced by the composite gels at the higher temperature did in fact lead to a higher dispersion (compare FIGS. 9A and 9B). The results with BSA, however, were inconclusive as no control/composite pair showed a set of measurable bandwidths.

The increased band dispersion in the composite hydrogels (a widening or lateral spreading of biomolecule within the gel), likely reflects macrovoids created within the matrix at temperatures above the lower critical solution temperature ("LCST"). The composite gels, at temperatures above the LCST, appear to illustrate the dual porosity that was emphasized above. This composite also illustrates the tunability of a gel based on system thermodynamics.

Mobility of Probes: Control vs. Composite Gels

The electrophoretic mobility results at room temperature (26° C.) for both OSA and BSA are shown for control gel (FIG. 8A) and the composite gel (FIG. 8B); the lane labeled "Mix" contains an equal volume mixture of BSA and OSA. The electrophoretic mobility results at higher temperature (34° C.) for both OSA and BSA are shown for control gel (FIG. 9A) and the composite gel (FIG. 9B); again, the lane labeled "Mix" contains an equal volume mixture of BSA and OSA. The distances that these probes traveled are also reported in TABLE 5. The mobility of OSA increased by a factor of 1.2 at room temperature in composite gels versus control gels. At the higher temperature, however, where PNIPAM microparticle collapse is expected, the mobility of OSA increased by a factor of 1.4 for composite gels versus control gels. This is consistent with the idea that greater void space—resulting from the collapse of PNIPAM microparticles—leads to reduced resistance to migration of biomolecules in the composite gel at higher temperatures. The increase in the mobility ratio indicates that that increased mobility of OSA is not solely the result of higher temperature, and that composite gel morphology is a significant contributing factor.

Again, the BSA data are inconclusive because of the lack of definition of the resulting bands in many cases. In fact, run 2 at the higher temperature does not show the same mobility ratio for either OSA or BSA and the replicate (n=2) data is attributed to a potential malfunction of the equipment.

Morphological Changes of the Composite Gel at High Temperature

At higher temperatures (above the PNIPAM LCST), the PNIPAM microparticles decrease in volume by about half due to incompatibility with the water in the hydrogel. For a 400 nm diameter particle, if the matrix does not adhere to the particle during shrinkage, one would expect a 200 nm void to be left behind. Indeed, as shown in FIG. 10B, the composite gel became opaque at higher temperature (34° C.), while the control gel (FIG. 10A) did not. This is evidence of light scattering caused by the voids left behind after PNIPAM microparticle collapse. The opacity is homogenous, and the bulk gel does not shrink (i.e., the gross dimensions of the gel

TABLE 5

Summary of Results

| Gel Type | T (° C.) | OSA Distance (cm) | OSA Width (cm) | BSA Distance (cm) | BSA Width (cm) | Gel Length (cm) | OSA Distance$_{Composite}$ / OSA Distance$_{Control}$ |
|---|---|---|---|---|---|---|---|
| Control Gel | 26 | 3.70 | 0.40 | 2.70 | NR* | 7.50 | 1.19 |
| Composite Gel | 26 | 4.40 | 0.10 | 2.00 | NR* | 7.20 | |
| Control Gel 1 | 34 | 4.5 | 0.40 | — | — | 7.30 | 1.40 |
| Composite Gel 1 | 34 | 6.32 | 0.25 | — | — | 8.00 | |
| Control Gel 2 | 34 | 2.50 | NR* | 2.70 | NR* | 7.80 | 1.20 |
| Composite Gel 2 | 34 | 3.00 | 0.20 | 1.30 | 0.2 | 7.40 | |

*NR = no resolution; the band had no distinct upper limit.

do not change), so no net movement of either the matrix or microparticles is expected (nor was it observed). In other words, the gel matrix "scaffold" is stable in relation to the dynamic microparticles—collapse of the microparticles does not appear to collapse or otherwise alter the gel matrix, other than by producing voids that had been filled by the expanded microparticles.

One might notice in the images of FIGS. 9A and 9B that the composite gel (FIG. 9B) is not opaque, as would be expected after performing electrophoresis at an elevated temperature (34° C.). After electrophoresis, however, both control (FIG. 9A) and composite (FIG. 9B) gels were returned to room temperature (26° C.) to take the photographs. Otherwise, the opaque composite gel would have scattered the UV light, interfering with the quality of the image and preventing visualization of the protein bands. This temperature reduction required only 1 to 2 minutes, and had no effect on the measured mobility of the protein bands in either gel.

Towards Improved Separation of Proteins in Tunable Composite Gels

In summary, the invention demonstrates band focusing in composite gels versus control gels at both the low (26° C.) and high (34° C.) temperature conditions. However, the composite gels at high temperature showed greater band dispersion than the composite gels at low temperature. This is attributable to an increased void size distribution at the higher temperature. In terms of OSA mobility, a difference in protein mobility was observed for composite gels versus control gels in all cases, with the OSA moving faster through the composite gels than through the control gels. The morphological change also resulted in a change in protein movement: the ratio of composite/control OSA movement was 1.2 for the swollen PNIPAM microparticles; and was 1.4 for the collapsed PNIPAM microparticles. The faster movement of OSA in the latter case is again attributed to a dual pore size distribution. Pores of 8 nm (inherent in the polyacrylamide gel) and voids of 200 nm (from collapsed microparticles) are present in this collapsed PNIPAM microparticle/PAGE composite gel.

Reproducibility

The reproducibility of OSA mobility in polyacrylamide control gels was established by synthesizing 5 gels and running OSA in at least 5 lanes per gel. For a 45-minute run at room temperature using 22 volts, the length of travel was 3.5 cm±1%, and band width was 0.56 cm±20%, as measured manually using a clear ruler.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A composite hydrogel, wherein the composite hydrogel comprises a thermally crosslinked hydrogel and a plurality of thermoresponsive microparticles.

2. The composite hydrogel of claim 1, wherein the thermally crosslinked hydrogel envelops substantially all of the thermoresponsive microparticles, and wherein the thermoresponsive microparticles are dispersed substantially uniformly throughout the thermally crosslinked hydrogel.

3. The composite hydrogel of claim 2, wherein the thermally crosslinked hydrogel is a polyacrylamide hydrogel.

4. The composite hydrogel of claim 3, wherein the thermoresponsive microparticles have a first diameter within a first temperature range and a second diameter within a second temperature range, wherein the first diameter is greater than the second diameter and the first temperature range is below the second temperature range.

5. The composite hydrogel of claim 4, wherein the first temperature range is between 0° C. and 31° C. and the second temperature range is from 31° C. to 60° C.

6. The composite hydrogel of claim 5, wherein the composite hydrogel further comprises voids when the second temperature range is between 31° C. and 60° C.

7. The composite hydrogel of claim 6, wherein the thermoresponsive microparticles are PNIPAM particles.

8. The composite hydrogel of claim 7, wherein the PNIPAM particles represent between greater than zero and 40% of the hydrogel by weight.

9. The composite hydrogel of claim 8, wherein the PNIPAM particles represent between greater than zero and 10% of the composite hydrogel by weight.

10. The composite hydrogel of claim 9, wherein the PNIPAM particles represent between greater than zero and 4% of the composite hydrogel by weight.

11. A method of making a thermoresponsive composite hydrogel, comprising the steps of:
    a) selecting thermoresponsive microparticles having a first diameter within a first temperature range, and a second diameter within a second temperature range;
    b) providing acrylamide, bis-acrylamide, a radical-producing agent, a chemical initiator, and water;
    c) mixing the microparticles, acrylamide, bis-acrylamide, and water;
    d) adding the radical-producing agent to the mixture, then adding the chemical initiator to the mixture.

12. The method of claim 11, wherein the first diameter is greater than the second diameter, and the first temperature range is below the second temperature range.

13. The method of claim 11, wherein the first temperature range is between 0° C. and 31° C. and the second temperature range is from 31° C. to 60° C.

14. The method of claim 11, wherein the thermoresponsive microparticles are PNIPAM particles, the radical-producing agent is ammonium persulfate, and the chemical initiator is N,N,N',N'-tetramethylethylenediamine.

15. The method of claim 14, wherein the PNIPAM particles represent between greater than zero and 40% of the thermoesponsive composite hydrogel by weight.

16. The method of claim 15, wherein the PNIPAM particles represent between greater than zero and 10% of the thermoresponsive composite hydrogel by weight.

17. The method of claim 16, wherein the PNIPAM particles represent between greater than zero and 4% of the thermoresponsive composite hydrogel by weight.

18. The method of claim 14, wherein Bis represents between greater than zero and 10% of the thermoresponsive composite hydrogel by weight.

19. The method of claim 18, wherein Bis represents between greater than zero and 6% of the thermoresponsive composite hydrogel by weight.

20. The method of claim 19, wherein Bis represents between 2% and 6% of the thermoresponsive composite hydrogel by weight.

21. A method of detecting a biomolecule, comprising the steps of:
   a) obtaining a thermoresponsive composite hydrogel comprising a thermally crosslinked hydrogel and a plurality of thermoresponsive microparticles, wherein the thermally crosslinked hydrogel envelops substantially all of the thermoresponsive microparticles, the thermoresponsive microparticles are dispersed substantially uniformly throughout the thermally crosslinked hydrogel, and wherein the thermoresponsive microparticles have a first diameter at a first temperature range and a second diameter at a second temperature range;
   b) subjecting the thermoresponsive composite hydrogel to a first tempertature;
   c) applying to the thermoresponsive composite hydrogel a solution, wherein the solution comprises at least one biomolecule to be detected;
   d) applying an electric field to the hydrogel;
   e) subjecting the hydrogel to a second temperature;
   f) removing the hydrogel from the electric field; and
   g) detecting the at least one biomolecule.

22. The method of claim 21, wherein the thermally crosslinked hydrogel is a polyacrylamide hydrogel, wherein the first diameter is greater than the second diameter, and wherein the first temperature range is below the second temperature range.

23. The method of claim 22, wherein the first temperature range is between 0° C. and 31° C. and the second temperature range is from 31° C. to 60° C.

24. The method of claim 23, wherein the thermoresponsive microparticles are PNIPAM particles.

25. The method of claim 24, wherein the PNIPAM particles represent between greater than zero and 40% of the thermoresponsive composite hydrogel by weight.

26. The method of claim 25, wherein the PNIPAM particles represent between greater than zero and 10% of the thermoresponsive composite hydrogel by weight.

27. The method of claim 26, wherein the PNIPAM particles represent between greater than zero and 4% of the thermoresponsive composite hydrogel by weight.

28. The method of claim 23, wherein Bis represents between greater than zero and 10% of the thermoresponsive composite hydrogel by weight.

29. The method of claim 28, wherein Bis represents between greater than zero and 6% of the thermoresponsive composite hydrogel by weight.

30. The method of claim 29, wherein Bis represents between 2% and 6% of the thermoresponsive composite hydrogel by weight.

* * * * *